United States Patent [19]

Chu et al.

[11] Patent Number: 5,043,512
[45] Date of Patent: Aug. 27, 1991

[54] ALKYLAROMATIC ISOMERIZATION PROCESS

[75] Inventors: Pochen Chu, Voorhees; Garry W. Kirker, Washington Township, Gloucester County, both of N.J.; John D. Kushnerick, Boothwyn, Pa.; David O. Marler, Deptford, N.J.

[73] Assignee: Mobil Oil Corp., Fairfax, Va.

[21] Appl. No.: 576,566

[22] Filed: Aug. 31, 1990

Related U.S. Application Data

[63] Continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................................. C07C 5/22
[52] U.S. Cl. .................................... 585/481; 585/480
[58] Field of Search ................................ 585/480, 481

[56] References Cited

U.S. PATENT DOCUMENTS

| | | | |
|---|---|---|---|
| Re. 30,157 | 11/1979 | Burress | 585/411 |
| Re. 31,782 | 12/1984 | Olson et al. | 585/481 |
| 3,856,871 | 12/1974 | Haag et al. | 260/668 A |
| 3,856,872 | 12/1974 | Morrison | 260/668 A |
| 4,100,214 | 7/1978 | Dwyer | 260/668 A |
| 4,101,595 | 7/1978 | Chen et al. | 260/668 A |
| 4,101,596 | 7/1978 | Mitchell et al. | 260/668 A |
| 4,101,597 | 7/1978 | Breckenridge | 260/668 A |
| 4,152,363 | 5/1979 | Tabak et al. | 585/481 |
| 4,158,676 | 6/1979 | Smith et al. | 585/481 |
| 4,159,282 | 6/1979 | Olson et al. | 585/481 |
| 4,159,283 | 6/1979 | Nicoletti et al. | 585/481 |
| 4,163,028 | 7/1979 | Tabak et al. | 585/481 |
| 4,188,282 | 2/1980 | Tabak et al. | 208/134 |
| 4,224,141 | 9/1980 | Morrison et al. | 208/134 |
| 4,351,979 | 9/1982 | Chester et al. | 585/481 |
| 4,385,195 | 5/1983 | Butter et al. | 585/481 |
| 4,783,569 | 11/1988 | Hussmann et al. | 585/481 |
| 4,826,667 | 5/1989 | Zones et al. | 423/277 |
| 4,954,324 | 9/1990 | Rubin et al. | 502/74 |
| 4,962,259 | 10/1990 | Sachtler et al. | 585/480 |
| 4,962,260 | 10/1990 | Sikkenga et al. | 585/481 |

FOREIGN PATENT DOCUMENTS 0231860 1/1987 European Pat. Off. .

*Primary Examiner*—Anthony McFarlane
*Attorney, Agent, or Firm*—Alexander J. McKillop; Charles J. Speciale; Dennis P. Santini

[57] ABSTRACT

A process is provided for converting feedstock alkylaromatic compounds by isomerization over a catalyst comprising MCM-22.

31 Claims, No Drawings

ALKYLAROMATIC ISOMERIZATION PROCESS

CROSS-REFERENCE TO RELATED APPLICATIONS

This application is a continuation-in-part of application Ser. No. 254,524, filed Oct. 6, 1988, now U.S. Pat. No. 4,954,325, which is a continuation-in-part of application Ser. No. 98,176, filed Sept. 18, 1987, now abandoned, which is a continuation-in-part of application Ser. No. 890,268, filed July 29, 1986, now abandoned.

BACKGROUND OF THE INVENTION

1. Field of the Invention

This invention relates to a process for converting feedstock comprising alkylaromatic compounds of from 8 to 50 carbon atoms, e.g. monocyclic alkyl-substituted benzene of from 8 to 30 carbon atoms, polycyclic, e.g. polyphenyl, compounds of from 12 to 50 carbon atoms, and mixtures thereof, to product comprising aromatic compounds which differs from said feedstock. The process comprises contacting, under isomerization conversion conditions, said feedstock with a catalyst comprising a synthetic, thermally stable, active form of crystalline material designated MCM-22.

2. Description of Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as $Ca/2$, $Sr/2$, Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by convenient symbols, as illustrated by zeolite ZSM-5 (U.S. Pat. No. 3,702,886).

The use of certain zeolites as catalyst components is taught in U.S. Pat. No. 4,305,808, for example.

The silica-to-alumina ratio of a given zeolite is often variable; for example, zeolite X (U.S. Pat. No. 2,882,244) can be synthesized with a silica-to-alumina ratio of from 2 to 3; zeolite Y (U.S. Pat. No. 3,130,007) from 3 to about 6. In some zeolites, the upper limit of silica-to-alumina ratio is virtually unbounded. Zeolite ZSM-5 is one such material wherein the silica-to-alumina ratio is at least 5. U.S. Pat. No. 3,941,871 (RE. No. 29,948) discloses a porous crystalline silicate made from a reaction mixture containing no deliberately added alumina and exhibiting an x-ray diffraction pattern characteristic of ZSM-5. U.S. Pat. Nos. 4,061,724; 4,073,865 and 4,104,294 describe crystalline silicates of varying alumina and metal content.

U.S. Pat. No. 4,380,685 teaches para-selective alkylation, transalkylation or disproportionation of a substituted aromatic compound to form a dialkylbenzene compound mixture over catalyst comprising zeolite characterized by a constraint index of 1 to 12 and a silica:alumina mole ratio of at least 12:1, the catalyst having thereon incorporated various metals and phosphorus. Other patents covering alkylation and transalkylation include U.S. Pat. Nos. 4,127,616, 4,361,713, 4,365,104, 4,367,359, 4,370,508 and 4,384,155. Toluene is converted to para-xylene in U.S. Pat. Nos. 3,965,207, 3,965,208, 3,965,209, 4,001,346, 4,002,698, 4,067,920, 4,100,215 and 4,152,364, to name a few. Alkylation with olefins is taught, for example, in U.S. Pat. Nos. 3,962,364 and 4,016,218 and toluene is disproportionated in, for example, U.S. Pat. Nos. 4,052,476, 4,007,231, 4,011,276, 4,016,219 and 4,029,716.

Isomerization of xylenes is taught in, for example, U.S. Pat. Nos. 3,856,871; 3,856,872; Re. 30,157; 4,100,214, 4,101,595; 4,101,596; 4,101,597; 4,152,363; 4,158,676; 4,159,282; 4,159,282; Re. 31,782; 4,163,028; 4,188,282; 4,224,141; 4,385,195; and 4,351,979. U.S. Pat. No. 4,826,667 shows isomerization of xylenes over catalyst comprising SSZ-25. Octafining for manufacture of p-xylene is referred to in "Advances in Petroleum Chemistry and Refining", Vol. 4. p. 433, 1961 (Interscience Publishers, N.Y.). See also U.S. Pat. Nos. 2,550,531 and 2,589,189.

SUMMARY OF THE INVENTION

The present invention relates to a novel process for converting feedstock comprising alkylaromatic compounds of from 8 to 50 carbon atoms selected from the group consisting of monocyclic alkyl-substituted benzene of from 8 to 30 carbon atoms, polycyclic, e.g. polyphenyl, compounds of from 12 to 50 carbon atoms and mixtures thereof under isomerization conditions to produce isomerization product comprising aromatic compounds which differs from said feedstock over a catalyst comprising crystalline silicate MCM-22.

DESCRIPTION OF SPECIFIC EMBODIMENTS

The entire contents of application Ser. No. 254,524, filed Oct. 6, 1988, now U.S. Pat. No. 4,954,325 is incorporated hereby by reference.

Feedstock aromatic compounds converted hereby include, as non-limiting examples, individually and in mixture monocyclic alkyl-substituted benzene of from 8 to 30 carbon atoms having the structure

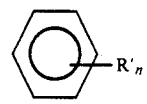

wherein R' is a $C_1$ to $C_{10}$ alkyl, methyl, ethyl, propyl or a combination thereof, and n is an integer of from 2 to 4. In other words, the feedstock aromatic compounds may be benzene containing from 2 to 4 methyl, ethyl and/or propyl group substituents, and mixtures thereof. Non-limiting examples of such feedstock compounds include xylene, diethylbenzene, diisopropylbenzene, mesitylene (1,3,5-trimethylbenzene), durene (1,2,4,5-tetramethylbenzene), pseudocumene (1,2,4-trimethylbenzene) and mixtures thereof.

Feedstock polycyclic, e.g. polyphenyl, aromatic compounds converted hereby include, as non-limiting examples, alkylbiphenyl, alkyldiphenylmethane, alkylnaphthalene, alkylanthracene, alkylstilbene and mixtures thereof.

In general, the present process is conducted at conversion conditions sufficient to convert the above feedstock to the indicated product including a temperature of from about 100° F. to about 1000° F., a pressure of from about 0 psig to about 1000 psig, a weight hourly space velocity of from about 0.1 $hr^{-1}$ to about 50 $hr^{-1}$ and a hydrogen/feedstock hydrocarbon compound mole ratio of from 0 (no added hydrogen) to about 10.

Such conversion process includes, as non-limiting examples, isomerizi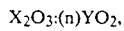 xylene feedstock components to product enriched in $p$-xylene and trimethylbenzene/ethyltoluene isomerization with preferred reaction conditions including a temperature from about 250° F. to about 950° F., a pressure of from about 25 psig to about 750 psig, a weight hourly space velocity of from about 0.5 $hr^{-1}$ to about 35 $hr^{-1}$ and a hydrogen/hydrocarbon mole ratio of from about 0.1 to about 7.5. Reaction conditions for this process may be maintained within the narrower ranges of from about 400° F. to about 900° F., from about 50 psig to about 500 psig a WHSV of from about 1 $hr^{-1}$ to about 25 $hr^{-1}$ and a hydrogen/hydrocarbon mole ratio of from about 0.5 to about 5.

The present process requires a catalyst comprising the synthetic, thermally stable, crystalline MCM-22. The high activity and unique selectivity of this catalyst for this process may be a result of its unique structure, its pore size and the nature and distribution of its active sites.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

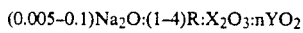

wherein R is an organic. The Na and R components are associated with the zeolite as a result of their presence during crystallization, and are easily removed by post-crystallization methods hereinafter more particularly described.

Zeolite MCM-22 is thermally stable and exhibits high surface area greater than 400 $m^2/gm$ as measured by the BET (Bruenauer, Emmett and Teller) test and unusually large sorption capacity when compared to previously described crystal structures having similar X-ray diffraction patterns. In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically the calcined MCM-22 may be characterized by an X-ray diffraction pattern including the following lines:

TABLE II

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstroms Units (A), corresponding to the recorded lines, were determined. In Tables I and II, the relative intensities are given in terms of the symbols W=weak, M=medium, S=strong and VS=very strong. In terms of intensities, these may be generally designated as follows:
W=0-20
M=20-40

S=40-60
VS=60-100

It should be understood that these X-ray diffraction patterns are characteristic of all species of zeolite MCM-22 The sodium form as well as other cationic forms reveal substantially the same pattern with some minor shifts in interplanar spacing and variation in relative intensity. Other minor variations can occur depending on the Y to X, e.g. silicon to aluminum, mole ratio of the particular sample, as well as its degree of thermal treatment.

Prior to its use as catalyst herein, the MCM-22 crystals should be subjected to thermal treatment to remove part or all of any organic constituent present therein. In addition, the zeolite MCM-22 crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g. sodium or potassium, cation, an oxide of trivalent element X, e.g aluminum, an oxide of tetravalent element Y, e.g. silicon, an organic (R) directing agent, e.g. hexamethyleneimine, and water, said reaction mixture having a composition, in terms of mole ratios of oxides, within the following ranges:

| Reactants | Useful | Preferred |
| --- | --- | --- |
| $YO_2/X_2O_3$ | 10-60 | 10-40 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g. at least about 30 wt. % solid $YO_2$. Where $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409, showing synthesis of PSH-3 compositions with hexamethyleneimine directing agent. If another source of oxide of silicon, e.g. Q-Brand (a sodium silicate comprised of about 28.8 wt. % of $SiO_2$, 8.9 wt. % $Na_2O$ and 62.3 wt. % $H_2O$) is used, crystallization may yield little, if any, MCM-22 crystalline material and impurity phases of other crystal structures, e.g. ZSM-12 may be produced Preferably therefore, the $YO_2$, e.g. silica, source contains at least about 30 wt. % solid $YO_2$, e.g. silica, and more preferably at least about 40 wt. % solid $YO_2$, e.g. silica.

Crystallization of the MCM-22 crystalline material can be carried out at either static or stirred conditions in a suitable reactor vessel, such as, e.g. polypropylene jars or teflon lined or stainless steel autoclaves. The total useful range of temperatures for crystallization is from about 80° C. to about 225° C. for a time sufficient for crystallization to occur at the temperature used, e.g. from about 25 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The MCM-22 crystals can be shaped into a wide variety of particle sizes, such as extrudate, beads or fluidizable microspheres. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It can be advantageous to incorporate the crystals of zeolite MCM-22 into some other materials, i.e. a matrix or binder, which is resistant to the temperature and other conditions employed in the present process. Useful matrix materials include both synthetic and naturally-occurring substances, e.g. inorganic materials such as clay, silica and/or metal oxides. Such materials can be either naturally-occurring or can be obtained as gelatinous precipitates or gels including mixtures of silica and metal oxides. Naturally-occurring clays which can be composited with MCM-22 include those of the montmorillonite and kaolin families, which families include the sub-bentonites and the kaolines commonly known as Dixie, McNamee, Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite catalyst can be composited with a porous metal oxide binder material such as alumina, titania, zirconia, silica, silica-alumina, silica-magnesia, silica-zirconia, silica-thoria, silica-beryllia, silica-titania, etc., as well as ternary oxides compositions such as silica-alumina-thoria, silica-alumina-zirconia, silica-alumina-magnesia, silica-magnesia-zirconia, etc. The binder material can be in the form of a cogel. It may be advantageous to provide at least part of the binder, e.g. an amount representing from 1 to 100 weight percent and preferably from about 2 to about 60 weight percent of the total binder material, in colloidal form so as to facilitate the extrusion of the zeolite bound therewith.

Since MCM-22 is synthesized nearly free of alkali metal ions, it can be used in the process of this invention without ion-exchange. To the extent desired, however, the original alkali metal ions, e.g. sodium, of the as-synthesized material can be replaced in accordance with techniques well known in the art, at least in part, by ion exchange with other ions. Preferred replacing ions include metal ions, hydrogen ions, hydrogen precursor, e.g. ammonium, ions and mixtures thereof. Particularly preferred ions are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

The synthetic porous crystalline MCM-22 present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the MCM-22 and/or matrix with which the MCM-22 may be optionally composited. Thus, for example, the hydrogenating component can be introduced into the catalyst composition by way of co-crystallization, exchanged into the composition to the extent a Group IIIA element, e.g. aluminum, is in the structure, impregnated therein or intimately physically admixed therewith. Such component can be impregnated in, or on, the synthetic porous crystalline material such as, for example, by, in the case of platinum, treating the synthetic porous crystalline material with a solution containing the platinum metal-containing ion. Thus, suitable platinum compounds for this purpose include chloroplatinic acid, platinous chloride and various compounds containing the platinum amine complex.

The stability of the zeolite catalyst may be increased by steaming, with suitable steam stabilization conditions including contacting the catalyst with, for example, 5-100% steam at a temperature of at least 300° C. (e.g. 300°-650° C.) for at least one hour (e.g. 1-200 hours) at a pressure of 100-2,500 kPa. In a more particular embodiment, the catalyst can be made to undergo steaming with 75-100% steam at 315°-500° C. and atmospheric pressure.

In order to more fully illustrate the process of this invention and the manner of practicing same, the following examples are presented. In examples illustrative of the synthesis of zeolite MCM-22, whenever sorption data are set forth for comparison of sorptive capacities for water, cyclohexane and/or n-hexane, they are Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078: in the *Journal of Catalysis*, vol. 4, p. 527 (1965): vol. 6, p. 278 (1966): and vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

EXAMPLE 1

One part of sodium aluminate (43.5% Al$_2$O$_3$, 32.2% Na$_2$O, 25.6% H$_2$O) was dissolved in a solution containing 1 part of 50% NaOH solution and 103.13 parts H$_2$O. To this was added 4.50 parts hexamethyleneimine. The resulting solution was added to 8.55 parts of Ultrasil, a precipitated, spray-dried silica (about 90% SiO$_2$).

The reaction mixture had the following composition, in mole ratios:

| | |
|---|---|
| SiO$_2$/Al$_2$O$_3$ = | 30.0 |
| OH$^-$/SiO$_2$ = | 0.18 |
| H$_2$O/SiO$_2$ = | 44.9 |
| Na/SiO$_2$ = | 0.18 |
| R/SiO$_2$ = | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table III. The sorption capacities of the calcined material were measured to be:

| | |
|---|---|
| H$_2$O (12 Torr) | 15.2 wt. % |
| Cyclohexane (40 Torr) | 14.6 wt. % |
| n-Hexane (40 Torr) | 16.7 wt. % |

The surface area of the calcined crystalline material was measured to be 494 m$^2$/g.

The chemical composition of the uncalcined material was determined to be as follows:

| Component | wt. % |
|---|---|
| SiO$_2$ | 66.9 |
| Al$_2$O$_3$ | 5.40 |
| Na | 0.03 |
| N | 2.27 |
| Ash | 76.3 |
| SiO$_2$/Al$_2$O$_3$, mole ratio = | 21.1 |

TABLE III

| Degrees 2-Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |

TABLE III-continued

| Degrees 2-Theta | Interplanar d-Spacing (A) | I/I$_o$ |
|---|---|---|
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days, respectively, in a stainless steel, stirred (350 rpm) autoclave at autogenous pressure. Solids were separated from any unreacted components by filtration and then water washed, followed by drying at 120° C. The product crystals were analyzed by X-ray diffraction, sorption, surface area and chemical analyses and the results are presented in Table IV. The sorption and surface area measurements were of the calcined product.

TABLE IV

| Example | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of MCM-22, 4.49 parts of hexamethyleneimine was added to a solution containing 1 part of sodium aluminate, 1 part of 50% NaOH solution and about 44.19 parts of $H_2O$. To the combined solution was added 8.54 parts of Ultrasil silica. The mixture was crystallized with agitation at 145° C. for 59 hours and the resultant product was water washed and dried at 120° C.

Product chemical composition (uncalcined), surface area and adsorption analyses results are set forth in Table V:

TABLE V

| Product Composition | | |
|---|---|---|
| C | 12.1 | wt. % |
| N | 1.98 | wt. % |
| Na | 640 | ppm |
| $Al_2O_3$ | 5.0 | wt. % |
| $SiO_2$ | 74.9 | wt. % |
| $SiO_2/Al_2O_3$, mole ratio | 25.4 | |
| Adsorption, wt. % | | |
| Cyclohexane | 9.1 | |
| n-Hexane | 14.9 | |
| $H_2O$ | 16.8 | |
| Surface Area, m$^2$/g | 479 | |

EXAMPLE 8

Twenty-five grams of solid crystal product from Example 7 were calcined in a flowing nitrogen atmosphere at 538° C. for 5 hours, followed by purging with 5% oxygen gas (balance $N_2$) for another 16 hours at 538° C.

Individual 3 g samples of the calcined material were ion-exchanged with 10 ml of 0.1N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of MCM-22 for different ions.

| Exchange Ions Ionic Comoosition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite has very good stability under severe hydrothermal treatment.

EXAMPLE 11

This example illustrates the preparation of MCM-22 where X in the general formula, supra, is boron. Boric acid, 2.59 parts, was added to a solution containing 1 part of 45% KOH solution and 42.36 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3$ = | 6.1 |
| $OH^-/SiO_2$ = | 0.06 |
| $H_2O/SiO_2$ = | 19.0 |
| $K/SiO_2$ = | 0.06 |
| $R/SiO_2$ = | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405 $m^2/g$.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3$ = | 12.3 |
| $OH^-/SiO_2$ = | 0.056 |
| $H_2O/SiO_2$ = | 18.6 |
| $K/SiO_2$ = | 0.056 |
| $R/SiO_2$ = | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ (12 Torr) | 14.4 wt. % |
| Cyclohexane (40 Torr) | 4.6 wt. % |
| n-Hexane (40 Torr) | 14.0 wt. % |

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 14

A portion of the calcined crystalline product of Example 13 was tested in the Alpha Test and found to have an Alpha Value of 5.

EXAMPLE 15

In another illustration of crystalline MCM-22 synthesis, 4.49 parts quantity of hexamethyleneimine was added to a mixture containing 1.00 part sodium aluminate, 1.00 part 50% NaOH, 8.54 parts Ultrasil VN3 and about 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried. The product zeolite was then calcined in nitrogen at 540° C., exchanged with aqueous ammonium nitrate and calcined in air at 540° C. The zeolite was tabletted, crushed and sized to 30/40 mesh. It had the following properties:

| | |
|---|---|
| Surface Area (BET), $m^2/g$ | 503 |
| $SiO_2/Al_2O_3$ (molar) | 27 |
| Na, ppm | 495 |
| Sorption Properties, wt. % | |
| $H_2O$ | 15.0 |
| $CyC_6$ | 12.5 |
| $n-C_6$ | 16.0 |
| Ash at 1000° C., wt. % | 99.05 |

EXAMPLE 16

In a glass reactor, a catalyst composed of a 0.2 gram sample of the product of Example 4, calcined in air for 3 hours, was heated to 500° F. A mixture of 1,3,5-triethylbenzene and benzene in 10/90 weight ratio was charged into the reactor at the rate of 2 ml/hour together with nitrogen carrier gas. Reaction conditions were maintained at 500° F., atmospheric pressure and 10 hr$^{-1}$ WHSV. The 1,3,5-triethylbenzene was in part isomerized to 1,2,4-triethylbenzene with conversion by isomerization measured to be 23%.

EXAMPLE 17

Catalysts prepared as in Example 15 were loaded into glass reactors and heated to 500° F. Liquid feedstock composed of 1,2,3-trimethylbenzene alone, and a 50/50 wt. mixture of 1,2,3-TMB and benzene were pumped into the reactors to provide a WHSV of 2 hr$^{-1}$. After 30 minutes on line, samples of the products provided the results listed in Table VI showing isomerization of the 1,2,3-TMB.

TABLE VI

Conversion of 1,2,3-TMB* over MCM-22

| Test Conditions | | |
|---|---|---|
| Temperature, °F. | 500 | 500 |
| Charge | 1,2,3-Trimethylbenzene | 50% 1,2,3-TMB 50% Benzene |
| WHSV, hr$^{-1}$ | 2 | 2 |
| TOS, min | 30 | 30 |
| Conv. of 1,2,3-TMB, wt. % | 90.7 | 93.8 |
| Products Dist. wt. % | | |
| C$_6$− | 0.21 | — |
| Benzene | — | 47.86 |
| Toluene | 0.42 | 4.26 |
| p-, m-Xylene | 2.16 | 1.33 |
| o-Xylene | 1.27 | 0.93 |
| 1,3,5-TMB | 20.27 | 12.33 |
| 1,2,4-TMB | 59.37 | 27.11 |
| 1,2,3-TMB | 9.32 | 3.12 |
| C$_{10}$+ | 6.98 | 3.15 |

*99.86% 1,2,3-TMB by analysis

EXAMPLE 18

A portion of the MCM-22 catalyst prepared in Example 15 was placed in the glass reactor and contacted with o-xylene feed at 500° F., atmospheric pressure and 10 hr$^{-1}$ WHSV. A product sample after 30 minutes on stream proved to comprise the following components (wt. %):

| Toluene | 0.78 |
|---|---|
| p-Xylene | 7.72 |
| m-Xylene | 26.26 |
| o-xylene | 64.62 |
| C$_9$+ | 0.61 |

EXAMPLE 19

A catalyst comprising 65% MCM-22 prepared as in Example 15 and 35% alumina binder was contacted with m-xylene feed at 600° F., atmospheric pressure and a WHSV of 3.4 hr$^{-1}$. Helium carrier gas was used at 2.1 moles He per mole of hydrocarbon. After 20 minutes on stream a sample of the product proved to comprise the following components (wt. %):

| Benzene | 0.02 |
|---|---|
| Toluene | 1.95 |
| m + p-Xylene | 77.46 |
| o-Xylene | 18.93 |
| C$_9$ Aromatics | 1.38 |

| -continued | |
|---|---|
| C$_{10}$+ Aromatics | 0.12 |

Selectivities for the process of this example were as follows (wt. %):

| (m + p)/(m + p + o)-Xylenes | 80.36 |
|---|---|
| o/(m + p + o)-Xylenes | 19.64 |
| o-Xylenes made/conv. | 83.96 |
| Aromatics (non-C$_8$)/o-Xylenes | 18.40 |

EXAMPLE 20

A sample of MCM-22 prepared as in Example 7 was combined with alumina to form a mixture of 65 parts by weight zeolite and 35 parts Al$_2$O$_3$. Water was added to this mixture to allow the resulting catalyst to be formed into extrudates. The catalyst was activated by calcining in nitrogen at 1000° F., followed by aqueous ammonium nitrate exchange and calcining in air at 1000° F. The resulting catalyst was then treated for 24 hours at 1150° F. in 100% steam. Platinum was incorporated into a portion of the steamed catalyst by adding an aqueous solution of Pt(NH$_3$)$_4$Cl$_2$ under partial vacuum in a rotovap. After the addition of the platinum solution was completed, the catalyst sample was mixed for 1 hour in a CO$_2$ atmosphere. After drying in air for 4 hours at room temperature and 16 hours at 240° F., the catalyst was calcined in 5v/v/min. air at 660° F. for 3 hours. It contained 0.97% Pt.

EXAMPLE 21

A portion of the catalyst prepared in Example 20 was sized and charged to a reactor and the feed described in Table VII was introduced at reaction conditions of 790° F., 200 psig, 10.0 hr$^{-1}$ WHSV and 2.5:1 H$_2$/HC molar ratio. After 12 hours the reaction product was analyzed. Table VIII summarizes the results of the product analysis. Ethylbenzene conversion proved to be 32.80%, xylene loss was only 11.44% and approach to p-xylene equilibrium was 101.1%.

TABLE VII

| Feed Component | Wt. % |
|---|---|
| Benzene | 0.00 |
| Toluene | 0.14 |
| Ethylbenzene | 12.01 |
| p-Xylene | 0.03 |
| m-Xylene | 45.04 |
| o-Xylene | 21.63 |
| C$_6$+ Nonaromatics | 21.14 |

TABLE VIII

| Product Component | Wt. % |
|---|---|
| C$_5$− | 10.45 |
| C$_6$+ Nonaromatics | 11.52 |
| Benzene | 1.74 |
| Toluene | 3.45 |
| Ethylbenzene | 8.07 |
| p-Xylene | 14.01 |
| m-Xylene | 31.44 |
| o-Xylene | 13.62 |
| Methylethylbenzene | 0.66 |
| Trimethylbenzene | 3.02 |
| Diethylbenzene | 0.61 |
| Dimethylethylbenzene | 1.56 |
| C$_{11}$+ Aromatics | 0.08 |

EXAMPLE 21

A sample of MCM-22 prepared as in Example 7 was combined with alumina to form a mixture of 65 parts by weight zeolite and 35 parts Al$_2$O$_3$. Water was added to this mixture to allow the resulting catalyst to be formed into extrudates. The catalyst was activated by calcining in nitrogen at 1000° F., followed by aqueous ammonium nitrate exchange and calcining in air at 1000° F.

EXAMPLE 22

A portion of the catalyst prepared in Example 21 was sized to 14/24 mesh and charged to a glass reactor. The reactor was preheated to 600° F. and the feed described in Table IX was introduced at reactor conditions of 5 hr$^{-1}$ WHSV, 0 psig and 100 cc/min N$_2$. After 1 hour on stream, liquid product was collected and analyzed. The results of this analysis are presented in Table X.

TABLE IX

| Feed Component | Wt. % |
| --- | --- |
| p-Ethyltoluene | 1.47 |
| m-Ethyltoluene | 1.56 |
| o-Ethyltoluene | 27.75 |
| 1,2,4-Trimethylbenzene | 8.32 |
| 1,3,5-Trimethylbenzene | 60.89 |

| | Wt. % |
| --- | --- |
| Product Component | |
| p-Ethyltoluene | 6.29 |
| m-Ethyltoluene | 3.35 |
| o-Ethyltoluene | 14.10 |
| 1,2,3-Trimethylbenzene | 5.25 |
| 1,2,4-Trimethylbenzene | 37.47 |
| 1,3,5-Trimethylbenzene | 27.25 |
| Conversion/Selectivity | |
| o-Ethyltoluene Conv. | 87.9% |
| p-Ethyltoluene Selectivity* | 51.4% |
| 1,3,5-Trimethylbenzene Conv. | 55.2% |
| 1,2,4-Trimethylbenzene Selectivity** | 86.7% |

*p-Ethyltoluene Selectivity = (wt. % p-Ethyltoluene Produced)/(wt. % o-Ethyltoluene Converted)
**1,2,4-Trimethylbenzene Selectivity = (wt. % 1,2,4-TMB Produced)/(wt. % 1,3,5-TMB Converted)

What is claimed is:

1. A process for catalytically converting feedstock alkylaromatic compounds of from 8 to 50 carbon atoms to product aromatic compounds which differ from said feedstock aromatic compounds which comprises contacting said feedstock at isomerization conversion conditions sufficient to convert said feedstock to said product with a catalyst composition comprising a catalytically effective amount of synthetic porous crystalline material characterized by an X-ray diffraction pattern substantially as set forth in Table I of the specification and having a composition comprising the molar relationship:

$$X_2O_3:(n)YO_2$$

wherein X is a trivalent element, Y is a tetravalent element and n is at least about 10.

2. The process of claim 1 wherein said synthetic porous crystalline material is characterized by an X-ray diffraction pattern substantially as set forth in Table II of the specification.

3. The process of claim 1 wherein X is selected from the group consisting of aluminum, boron, iron, gallium and combinations thereof and Y is selected from the group consisting of silicon, germanium and combinations thereof.

4. The process of claim 1 wherein X comprises aluminum and Y comprises silicon.

5. The process of claim 1 wherein said crystalline material has been treated to replace original ions, at least in part, with an ion or mixture of ions selected from the group consisting of hydrogen, hydrogen precursors, rare earth metals, and metals of Groups IIA, IIIA, IVA, IB, IIB, IIIB, IVB, VIB and VIII of the Periodic Table.

6. The process of claim 1 wherein said catalyst composition has been thermally treated in the presence or absence of steam at a temperature up to about 925° C.

7. The process of claim 5 wherein said catalyst composition has been thermally treated in the presence or absence of steam at a temperature up to about 925° C.

8. The process of claim 1 wherein said catalyst composition comprises a matrix material selected from the group consisting of alumina, silica, zirconia, titania, thoria, beryllia, magnesia and combinations thereof.

9. The process of claim 8 wherein said catalyst composition is in the form of extrudate, beads or fluidizable microspheres.

10. The process of claim 1 wherein said conversion conditions include a temperature of from about 100° F. to about 1000° F., a pressure of from about 0 psig to about 1000 psig, a weight hourly space velocity of from about 0.1 hr$^{-1}$ to about 50 hr$^{-1}$ and a hydrogen/feedstock hydrocarbon compound mole ratio of from 0 to about 10.

11. A process for catalytically converting feedstock monocyclic alkyl-substituted benzene of from 8 to 30 carbon atoms to isomerization conversion product which comprises contacting said feedstock at conversion conditions sufficient to convert said feedstock to said product with a catalyst composition comprising a catalytically effective amount of synthetic porous crystalline material characterized by an X-ray diffraction pattern substantially as set forth in Table I of the specification an having a composition comprising the molar relationship:

$$X_2O_3:(n)YO_2$$

wherein X is a trivalent element, Y is a tetravalent element and n is at least about 10.

12. The process of claim 11 wherein said synthetic porous crystalline material is characterized by an X-ray diffraction pattern substantially as set forth in Table II of the specification.

13. The process of claim 11 wherein X is selected from the group consisting of aluminum, boron, iron, gallium and combinations thereof and Y is selected from the group consisting of silicon, germanium and combinations thereof.

14. The process of claim 11 wherein X comprises aluminum and Y comprises silicon.

15. The process of claim 11 wherein said crystalline material has been treated to replace original ions, at least in part, with an ion or mixture of ions selected from the group consisting of hydrogen, hydrogen precursors, rare earth metals, and metals of Groups IIA, IIIA, IVA, IB, IIB, IIIB, IVB, VIB and VIII of the Periodic Table.

16. The process of claim 11 wherein said catalyst composition has been thermally treated in the presence or absence of steam at a temperature up to about 925° C.

17. The process of claim 15 wherein said catalyst composition has been thermally treated in the presence or absence of steam at a temperature up to about 925° C.

18. The process of claim 11 wherein said catalyst composition comprises a matrix material selected from the group consisting of alumina, silica, zirconia, titania, thoria, beryllia, magnesia and combinations thereof.

19. The process of claim 11 wherein said feedstock comprises xylenes.

20. The process of claim 11 wherein said feedstock comprises a component selected from the group consisting of diethylbenzene, diisopropylbenzene, mesitylene, durene, pseudocumene and mixtures thereof.

21. The process of claim 11 wherein said conversion conditions include a temperature of from about 250° F. to about 950° F., a pressure of from about 25 psig to about 750 psig, a weight hourly space velocity of from about 0.5 hr$^{-1}$ to about 35 hr$^{-1}$ and a hydrogen/hydrocarbon mole ration of from about 0.1 to about 7.5.

22. A process for catalytically converting feedstock polycyclic compounds of from 12 to 50 carbon atoms to isomerization conversion product which comprises contacting said feedstock at isomerization conversion conditions sufficient to convert said feedstock to said product with a catalyst composition comprising a catalytically effective amount of synthetic porous crystalline material characterized by an X-ray diffraction pattern substantially as set forth in Table I of the specification and having a composition comprising the molar relationship:

$$X_2O_3:(n)YO_2$$

wherein X is a trivalent element, Y is a tetravalent element and n is at least about 10.

23. The process of claim 22 wherein said synthetic porous crystalline material is characterized by an X-ray diffraction pattern substantially as set forth in Table II of the specification.

24. The process of claim 22 wherein X is selected from the group consisting of aluminum, boron, iron, gallium and combinations thereof and Y is selected from the group consisting of silicon, germanium and combinations thereof.

25. The process of claim 22 wherein X comprises aluminum and Y comprises silicon.

26. The process of claim 22 wherein said crystalline material has been treated to replace original ions, at least in part, with an ion or mixture of ions selected from the group consisting of hydrogen, hydrogen precursors, rare earth metals, and metals of Groups IIA, IIIA, IVA, IB, IIB, IIIB, IVB, VIB and VIII of the Periodic Table.

27. The process of claim 22 wherein said catalyst composition has been thermally treated in the presence or absence of steam at a temperature up to about 925° C.

28. The process of claim 26 wherein said catalyst composition has been thermally treated in the presence or absence of steam at a temperature up to about 925° C.

29. The process of claim 22 wherein said catalyst composition comprises a matrix material selected from the group consisting of alumina, silica, zirconia, titania, thoria, beryllia, magnesia and combinations thereof.

30. The process of claim 22 wherein said feedstock comprises a component selected from the group consisting of alkylbiphenyl, alkyldiphenylmethane, alkylstilbene, alkylnaphthalene, alkylanthracene and mixtures thereof.

31. The process of claim 22 wherein said conversion conditions include a temperature of from about 250° F. to about 950° F., a pressure of from about 25 psig to about 750 psig, a weight hourly space velocity of from about 0.5 hr$^{-1}$ to about 35 hr$^{-1}$ and a hydrogen/hydrocarbon mole ratio of from about 0.1 to about 7.5.

* * * * *

UNITED STATES PATENT AND TRADEMARK OFFICE
CERTIFICATE OF CORRECTION

PATENT NO. : 5,043,512

DATED : August 27, 1991

INVENTOR(S) : P. Chu et al.

It is certified that error appears in the above-identified patent and that said Letters Patent is hereby corrected as shown below:

Col. 2, line 33, "4,159,282" (second occurrence) should be --4,159,283--

Signed and Sealed this

Twenty-second Day of December, 1992

Attest:

DOUGLAS B. COMER

Attesting Officer      Acting Commissioner of Patents and Trademarks